(12) United States Patent
Brunelli et al.

(10) Patent No.: US 11,141,223 B2
(45) Date of Patent: Oct. 12, 2021

(54) APPARATUS AND METHOD FOR CALIBRATING AND MEASURING TARGET POINTS FOR CEREBRAL NEURO-NAVIGATORS

(71) Applicant: EB NEURO S.P.A., Florence (IT)

(72) Inventors: Cristian Brunelli, Grezzani (IT); Marco Rossi, Verona (IT)

(73) Assignee: EB Neuro S.P.A., Florence (IT)

( * ) Notice: Subject to any disclaimer, the term of this patent is extended or adjusted under 35 U.S.C. 154(b) by 426 days.

(21) Appl. No.: 16/182,014

(22) Filed: Nov. 6, 2018

(65) Prior Publication Data
US 2020/0138524 A1 May 7, 2020

(30) Foreign Application Priority Data
Nov. 6, 2017 (IT) .......................... 102017000125897

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61B 90/39* (2016.02); *A61B 5/0042* (2013.01);
(Continued)

(58) Field of Classification Search
CPC ...... A61B 2034/107; A61B 2034/2055; A61B 2034/2068; A61B 2090/3937; A61B 2560/0223; A61B 34/10; A61B 34/20; A61B 90/39; A61B 2017/00207; A61B 5/0042
See application file for complete search history.

(56) References Cited

U.S. PATENT DOCUMENTS 5,676,673 A * 10/1997 Ferre ...................... A61B 90/39
606/130
5,682,886 A * 11/1997 Delp .................... A61B 17/154
128/920

(Continued)

*Primary Examiner* — Amelie R Davis
(74) *Attorney, Agent, or Firm* — Shuttleworth & Ingersoll, PLC; Timothy J. Klima

(57) ABSTRACT

Described is an apparatus for calibrating or measuring target points (1) for cerebral neuro-navigators, comprising a processor (2) comprising a video output (3) on which can be displayed a preloaded three-dimensional or two-dimensional map (4) of a brain of a patient, a rigid body (5) comprising a plurality of optical markers (6) and a supporting tip (7) designed to be rested on the head of the patient and a stereoscopic video camera (8) configured to detect a position of the optical markers (6) relative to the head of the patient at a preset point (9) of the head of the patient and sending the position to the processor (2) to allow the acquisition of the preset point (9). The stereoscopic video camera (8) is configured for detecting and sending to the processor (2) static positions and movements of the optical markers (6). The processor (2) is also configured for acquiring the position of the preset point (9) when the movements of the optical markers (6) fall within a preset range of movement (10) for the entire duration of a preset time interval (11).

10 Claims, 1 Drawing Sheet

(51) Int. Cl.
*A61B 90/00* (2016.01)
*A61B 17/00* (2006.01)
*A61B 5/00* (2006.01)

(52) U.S. Cl.
CPC ............... *A61B 2017/00207* (2013.01); *A61B 2034/107* (2016.02); *A61B 2034/2055* (2016.02); *A61B 2090/3937* (2016.02); *A61B 2560/0223* (2013.01)

(56) References Cited

U.S. PATENT DOCUMENTS

2017/0265947 A1* 9/2017 Dyer .................. G16H 40/63
2018/0036884 A1* 2/2018 Chen .................. A61B 34/20

* cited by examiner

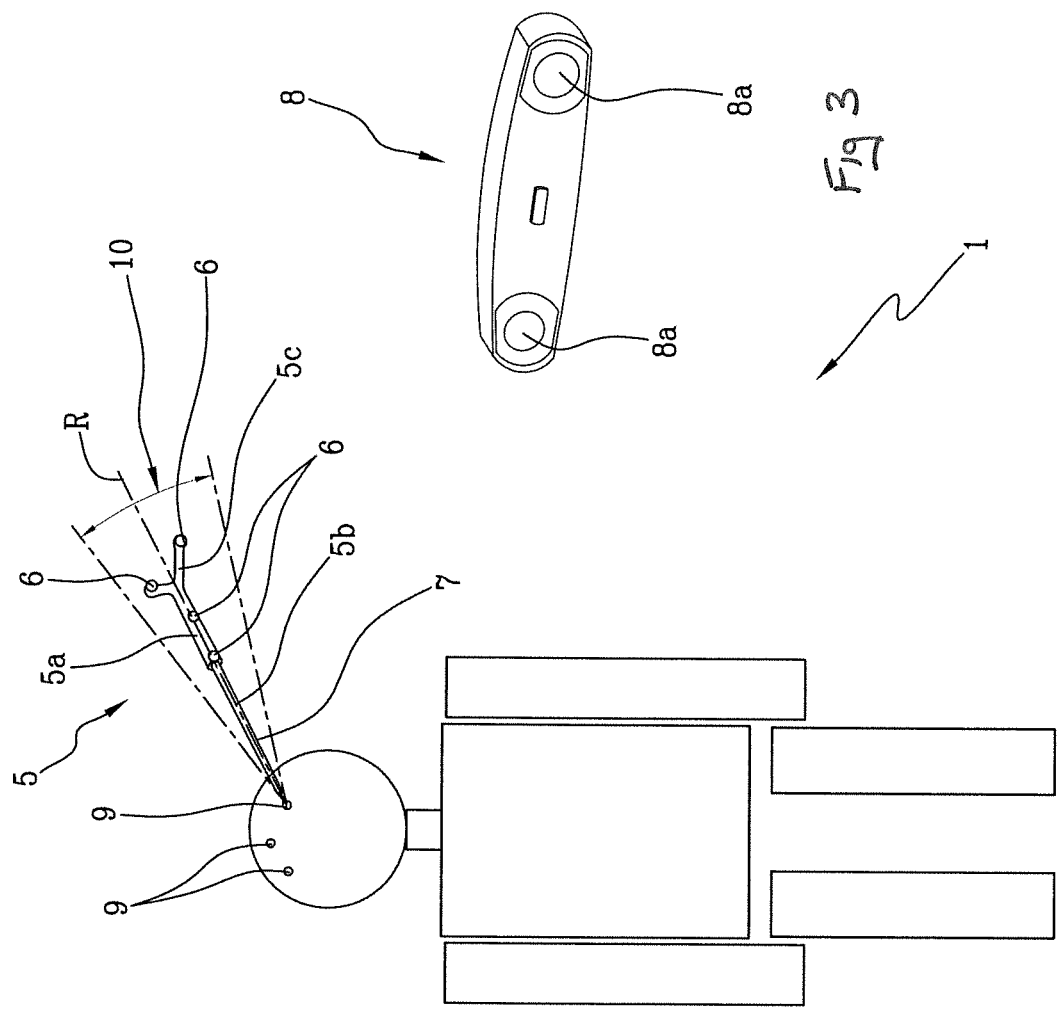
Fig 3
Fig. 2
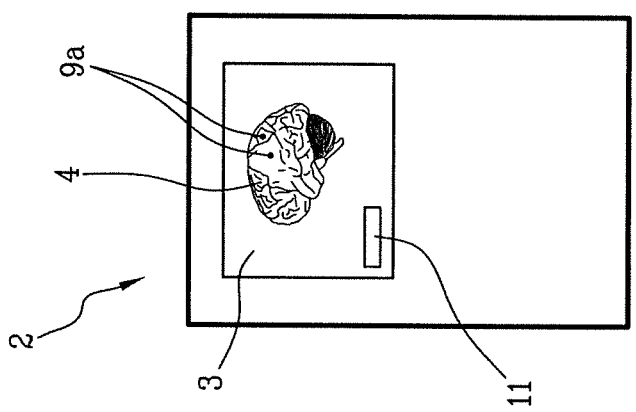
Fig.1

US 11,141,223 B2

APPARATUS AND METHOD FOR CALIBRATING AND MEASURING TARGET POINTS FOR CEREBRAL NEURO-NAVIGATORS

CROSS REFERENCE TO RELATED APPLICATION(S)

This application relates to, and claims priority from, Italian Ser. No. IT-102017000125897 filed Nov. 6, 2017, the entire contents of which is incorporated herein by reference.

DESCRIPTION

BACKGROUND OF THE INVENTION

This invention relates to an apparatus for calibrating and measuring target points for cerebral neuro-navigators.

This invention relates to a calibration method for cerebral neuro-navigators.

The term cerebral neuro-navigators is used to mean devices whose purpose is to allow the navigation in a two-dimensional or three-dimensional map of a brain of a patient by means of a monitor of a processor.

In more detail, a cerebral neuro-navigator makes it possible to display on a screen the map of the brain of the patient, which has been previously produced and loaded in the processor by magnetic resonance or other similar methods, and therefore be able to display the reactions following suitable operations carried out on the patient (such as, for example, stimulations of various types or nerve conduction velocity tests).

In order to be able to perform these operations it is firstly necessary to calibrate the map of the patient's brain, detecting at least three points on the head of the patient in such a way that a movement of the head of the patient corresponds to a movement of the three-dimensional map on the screen of the processor.

The detection of the at least three points on the head of the patient is carried out by means of specific devices which, in addition to the acquisition, also allow movements of the head of the patient to be detected and to reproduce them on the processor screen by means of the map. The measurement of these movements makes it possible to perform the above-mentioned tests.

The prior art devices for calibrating or measuring target points comprise the use of an apparatus equipped with optical markers and at least one stereoscopic video camera designed to detect the optical markers.

In practice, the calibration reference is rested on the head of the patient in one of the points of the head to be acquired and the stereoscopic video camera starts acquiring the position of the optical markers with respect to the head of the patient.

This acquisition occurs by means of a pedal installed on the processor which must be pressed by an operator who, usually, is the same operator who must rest the calibration reference on the head of the patient.

Disadvantageously, this leads to a not very precise acquisition of the predetermined points following the simultaneous movement and action of the two functions which the operator must perform in order to press the pedal, thus generating undesired shaking of the apparatus to be rested on the head of the patient.

Moreover, the presence of the pedal forces a predetermined positioning of the video camera and of the processor which leads to various inconvenient obstructions both for the operator and for the patient since a working position is created in which the movements (both of the operator and of the patient) are limited. In other words, the video camera must be positioned in such a way as to capture the optical markers whilst the processor is sufficiently close to the operator in such a way that the latter can press the pedal.

Disadvantageously, in order to obtain an acquisition which is as precise as possible, it is necessary to keep the calibration reference rested on the head of the patient for a long time, creating a situation which is not very comfortable for the patient.

Disadvantageously, if there is a poor accuracy of the point to be detected a second pedal is necessary, whose aim is to delete the point acquired, thus increasing the obstacles and limiting the movements of the patient and the operator.

The technical purpose of the invention is therefore to provide an apparatus and a method for calibrating cerebral neuro-navigators which are able to overcome the drawbacks of the prior art.

The aim of the invention is thus to provide an apparatus and a method for calibrating cerebral neuro-navigators which allows precise predetermined points to be acquired which is not very invasive for the patent.

Another aim of this invention is to provide an apparatus and a method for calibrating cerebral neuro-navigators which reduce the overall dimensions for the patient and for the operator in such a way as to allow a certain freedom of movement for both.

The technical purpose indicated and the aims specified are substantially achieved by an apparatus and a method for calibrating cerebral neuro-navigators comprising the technical features described in one or more of the appended claims.

Further features and advantages of the invention are more apparent in the non-limiting description which follows of a preferred embodiment of an apparatus and a method for calibrating cerebral neuro-navigators.

BRIEF DESCRIPTION OF THE DRAWINGS

The description is set out below with reference to the accompanying drawings, which are provided solely for purposes of illustration without restricting the scope of the invention and in which:

FIGS. 1-3 are a schematic illustrative views of a calibration apparatus and elements according to the invention.

DETAILED DESCRIPTION OF THE INVENTION

With reference to the accompanying drawings, the numeral 1 denotes a calibration apparatus for cerebral neuro-navigators which, for simplicity, will hereinafter be referred to as the calibration apparatus 1.

The calibration apparatus 1 comprises a processor 2 equipped with a video outlet 3 which, in the accompanying drawing, is integrated in the processor 2 (but the video outlet 3 can also be a screen separated from the processor 2).

The video output 3 allows a preloaded three-dimensional map 4 of a brain of a patient to be displayed. The preloaded three-dimensional map 4 can be obtained by means of magnetic resonance or other similar means and is loaded in the processor 2 to allow an operator (whether it is a doctor or other skilled technician) to have a three-dimensional view of the brain of the patient.

The calibration apparatus 1 also comprises a rigid body 5 equipped with a plurality of optical markers 6 (four optical markers 6 are shown in FIG. 1) and a supporting tip 7 designed to be rested on the head of the patient.

Preferably, as shown in FIG. 1, the rigid body 5 is made in the form of a pen 5a comprising in a first end 5b the supporting tip 7 and in a second end 5c, opposite the first end 5b, the plurality of optical markers 6.

In other words, the plurality of optical markers 6 are opposite the supporting tip 7 in such a way as to be sufficiently spaced from the head of the patient.

The calibration apparatus 1 also comprises a stereoscopic video camera 8 equipped with suitable parallel lenses 8a configured to film and to reproduce three-dimensional images.

The stereoscopic video camera 8 is configured for measuring a position of the optical markers 6 relative to the head of the patient. The optical markers 6 are sufficiently spaced from the head of the patient to be detected easily by the stereoscopic video camera 8 without there being obstruction from, for example, hair of the patient or the hand of the operator.

In other words, the stereoscopic video camera 8, as it is capable of detecting three-dimensional images, is preferably able to acquire the image of the head of the patient and to associate it with the preloaded three-dimensional map 4 and therefore to recognise the position of the rigid body 5, and the software on the processor is able to reconstruct the position of the head of the patient knowing the position of the markers with respect to the head of the patient.

The stereoscopic video camera 8 is also capable of detecting movements of the optical markers 6 relative to an initial reference position "R" (the meaning of initial reference position will be described in more detail below).

Preferably, the video camera is able to detect the position and the movements of a rigid body supporting markers, connected to the head of the patient.

The stereoscopic video camera 8 is designed to send the position and the movements of the optical markers 6 sending them to the processor 2 to allow the acquisition of a preset point 9 of the head of the patient to identify an orientation of the preloaded three-dimensional map 4.

In other words, the operator identifies at least the three points to be acquired of the head of the patient and enters these points in the processor 2 displaying them on the preloaded three-dimensional map 4 (alternatively, the operator may mark the preset points 9 on the head of the patient to help in their acquisition).

According to the invention, each preset point 9 is acquired when certain conditions occur. More specifically, each preset point 9 is acquired when the position of the rigid body 5 corresponds to the desired preset point 9 (or in any case falls within an acceptable area for the purposes of calibration) and when the movements of the optical markers 6 fall within a preset range of movement 10 for the entire duration of a preset time interval 11. If even only one of the above-mentioned three conditions does not occur, the preset point 9 is not acquired.

The initial reference position "R" corresponds to the position of the rigid body 5 at the initial instant when this rests, with its supporting tip 7, on the head of the patient in the preset point 9.

Preferably, the preset range of movement 10 is between 0.1 mm and 1 mm; even more preferably, the preset range of movement 10 is close to zero when the operator is confident in his/her capacity to maintain the rigid body 5 stationary.

The initial reference point "R" is reset when the movements of the rigid body 5 exceed the preset range of movement 10 within the expiry of the preset time interval 11. In other words, as well as preventing the acquisition of the preset point 9, not complying with the preset range of movement 10 causes a reset of the acquisition of the preset point 9.

Preferably, the preset time interval 11 (the progress of which can be displayed on the video output 3) is between 0.5 and 4 seconds. Even more preferably, the preset time interval 11 is one second (the ideal solution to prevent annoying increases in time both for the operator and for the patient during acquisition of the preset point 9).

Both the ranges have been previously decided upon by the operator on the basis of the precision of the desired acquisition.

The acquisition of at least three preset points 9 makes it possible to orient the preloaded three-dimensional map 4, thus creating a synchronism between the movements of the preloaded three-dimensional map 4 and the head of the patient. Consequently, an increase in the preset points 9 to be acquired leads to a greater accuracy in the movements of the preloaded three-dimensional map 4 with respect to the head of the patient.

Preferably, the calibration apparatus 1 (more specifically, the processor 2) also allows the position of a preset point 9 previously acquired by a predetermined movement of the rigid body 5 to be deleted.

In other words, it is possible to execute this deletion command by shaking the rigid body 5 according to a movement previously established and recorded in the processor 2 and at a certain speed which identifies the effective desire by the operator to execute the deletion action.

Preferably, the processor 2 is also configured to assign a plurality of functions of the calibration apparatus 1 to corresponding movements of the rigid body 5.

In other words it is possible to assign other commands to specific movements of the rigid body 5.

For example, it is possible to assign a movement similar to that described above for deleting in one operation all the points 9 acquired, if desired by the operator.

The correct use of the calibration apparatus 1 as described above will be more clearly understood from the following description of a calibration method for cerebral neuro-navigators.

The calibration method comprises: A) preparing a processor 2 on which can be displayed a preloaded three-dimensional map 4 of a brain of a patient, B) selecting on the preloaded three-dimensional map 4 at least three reference points 9a, C) preparing a rigid body 5, comprising a plurality of optical markers 6 and a supporting tip 7 designed to be rested on the head of the patient, and D) preparing a stereoscopic video camera 8.

The method comprises: E) resting the supporting tip 7 of the rigid body 5 on the head of the patient in one of the preset points 9 corresponding to one of the reference points 9a.

Subsequently, the method comprises: F) detecting a position of the optical markers 6 with the stereoscopic video camera 8 and G) detecting, again with the stereoscopic video camera 8, movements of the optical markers 6 relative to an initial reference position "R".

Simultaneously with steps F) and G) the step H) is performed for sending the position and the movements from the stereoscopic video camera 8 to the processor 2.

This is followed by step I) for acquiring the preset point 9 with the processor 2 for identifying the orientation of the preloaded three-dimensional map 4.

More specifically, the step I) comprises the sub-steps of: (I1)) comparing the movements of the optical markers 6 with a preset range of movement 10 for the entire duration of a preset time interval 11 and (I2)) acquiring the position of the preset point 9 when the movements fall within the preset range of movement 10 for the entire duration of the preset time interval 11. The acquisition step is followed by step J), repeating steps E) to I) for each reference point (9a). In other words, the steps E) to I) are repeated until obtaining at least three preset points 9 of the head of the patient.

If the step B) comprises entering a greater number of reference points 9a (with respect to three), to obtain a more accurate and precise orientation of the preloaded three-dimensional map 4, the steps E) to I) are repeated for the same number of times before allowing a movement of the preloaded three-dimensional map 4 following the movement of the head by the patient.

Preferably, the calibration method comprises the step K) for deleting the preset point 9 acquired when the acquiring step I) does not provide a sufficiently precise result (where the expression, a not sufficiently precise result, means a result which, to the operator, does not satisfy the requirements to make a precise calibration between the movements of the preloaded three-dimensional map 4 and the movements of the head of the patient).

Still more preferably, the deleting step K) comprises shaking the rigid body 5 in such a way that the stereoscopic video camera 8 can identify a predetermined movement of the rigid body 5 associated with the command to delete the preset point 9 acquired.

Preferably, the calibration method also comprises the step of resetting L) the position of the initial reference point "R" when the movements exceed the preset range of movement 10 within the expiry of the preset time interval 11.

Advantageously, the calibration apparatus 1 and the calibration method described above allow the drawbacks of the prior art to be overcome.

More specifically, the calibration apparatus 1 allows precise predetermined points to be acquired which are not very invasive for the patent.

Advantageously, the apparatus 1 according to this invention makes it possible to easily delete acquisitions considered not very precise and to repeat the acquisition operation without discomfort for the patient.

Still more advantageously, the calibration apparatus 1 according to the invention makes it possible to reduce the obstructions for the patient and for the operator which would otherwise be present with the prior art calibration apparatuses. More specifically, the calibration apparatus 1 allows a certain freedom of movement both for the operator and the patient which are not constrained by pedals or by dimensions caused by the arrangement of the processor and the stereoscopic video camera.

The invention claimed is:

1. An apparatus for calibrating a map of a brain of a patient, comprising:
    a processor comprising a video output configured for displaying a preloaded three-dimensional map of the brain of the patient, wherein the preloaded three-dimensional map includes at least three reference points;
    a rigid body comprising a plurality of optical markers and a supporting tip configured to be rested on a head of the patient;
    a stereoscopic video camera configured for:
        detecting a position of the optical markers relative to the head of the patient at a preset point of the head of the patient corresponding to one of the at least three reference points and sending the position to the processor to allow the acquisition of the preset point;
        detecting and sending to the processor movements of the optical markers relative to an initial reference position;
    wherein the processor is configured for:
        acquiring the position of the preset point for identifying an orientation of the preloaded three-dimensional map, the acquiring including:
            comparing the movements of the optical markers with a preset range of movement for an entire duration of a preset time interval;
            acquiring the position of the preset point when the movements of the optical markers fall within the preset range of movement for the entire duration of the preset time interval;
        deleting a position of a previously acquired preset point based on a predetermined movement of the rigid body;
    wherein the stereoscopic video camera and the processor are further configured for repeating the detecting and sending the position of the optical markers, the detecting and sending the movements of the optical markers and the acquiring the position of the preset point for each of the at least three reference points, thereby calibrating the map of the brain of the patient.

2. The apparatus according to claim 1, wherein the preset range of movement is between 0.1 mm to 1 mm.

3. The apparatus according to claim 1, wherein: the processor is further configured for resetting the initial reference position when the movements exceed the preset range of movement within the preset time interval.

4. The apparatus according to claim 1, wherein the preset time interval is between 0.5 and 4 seconds.

5. The apparatus according to claim 1, wherein the rigid body includes a first end, including the supporting tip and a second end, opposite the first end, including the plurality of optical markers.

6. The apparatus according to claim 1, wherein the processor is further configured for assigning a plurality of functions of the apparatus to respective predetermined movements of the rigid body.

7. The apparatus according to claim 1, wherein the preset time interval is one second.

8. A method for calibrating a map of a brain of a patient, comprising the steps of:
    calibrating the map of the brain of the patient by:
    A) preparing a processor configured for displaying a preloaded three-dimensional map of the brain of the patient;
    B) selecting on the preloaded three-dimensional map at least three reference points;
    C) preparing a rigid body comprising a plurality of optical markers and a supporting tip configured to be rested on a head of the patient;
    D) preparing a stereoscopic video camera;
    E) resting the supporting tip of the rigid body on the head of the patient at a preset point corresponding to one of the at least three reference points;
    F) measuring a position of the optical markers with the stereoscopic video camera;
    G) measuring movements of the optical markers relative to an initial reference position with the stereoscopic video camera;
    H) sending the position and the movements from the stereoscopic video camera to the processor;
    I) acquiring the position of the preset point with the processor for identifying an orientation of the preloaded three-dimensional map, the step of acquiring the position of the preset point comprising the sub-steps of:
- I1) comparing the movements of the optical markers with a preset range of movement for an entire duration of a preset time interval;
- I2) acquiring the position of the preset point when the movements fall within the preset range of movement for the entire duration of the preset time interval;
- J) repeating steps E) to I) for each reference point; and
- K) deleting a position of a previously acquired preset point based on a predetermined movement of the rigid body.

9. The method according to claim 8, also comprising the step of: L) resetting the position of the initial reference position when the movements exceed the preset range of movement within the preset time interval.

10. The method according to claim 8, wherein the step K) is performed by shaking the rigid body.

* * * * *